(12) United States Patent
Watanabe et al.

(10) Patent No.: US 11,585,781 B2
(45) Date of Patent: Feb. 21, 2023

(54) GAS SENSOR

(71) Applicant: NGK INSULATORS, LTD., Aichi (JP)

(72) Inventors: Yusuke Watanabe, Nagoya (JP); Shotaro Niizuma, Kasugai (JP); Hayami Aota, Nagoya (JP); Toshihiro Hirakawa, Kasugai (JP)

(73) Assignee: NGK INSULATORS, LTD., Nagoya (JP)

( * ) Notice: Subject to any disclaimer, the term of this patent is extended or adjusted under 35 U.S.C. 154(b) by 84 days.

(21) Appl. No.: 17/002,942

(22) Filed: Aug. 26, 2020

(65) Prior Publication Data

US 2021/0063342 A1    Mar. 4, 2021

(30) Foreign Application Priority Data

Aug. 28, 2019  (JP) .............................. JP2019-155211

(51) Int. Cl.
*G01N 27/406* (2006.01)
*G01N 27/407* (2006.01)
*G01N 33/00* (2006.01)

(52) U.S. Cl.
CPC ..... *G01N 27/4062* (2013.01); *G01N 27/4071* (2013.01); *G01N 33/0037* (2013.01)

(58) Field of Classification Search
CPC ........ G01N 27/406–41; G01N 33/0004–0075; G01N 27/4078; G01N 27/407; G01N 27/409; G01N 27/4062; G01N 27/4071; G01N 27/4074; G01N 27/4075; G01N 27/4076; G01N 27/419; G01N 33/0037; G01N 33/0054
See application file for complete search history.

(56) References Cited

U.S. PATENT DOCUMENTS

| | | | |
|---|---|---|---|
| 6,164,120 A | 12/2000 | Friese et al. | |
| 7,469,586 B2 * | 12/2008 | Wild | G01N 27/4062 73/431 |
| 9,525,280 B2 * | 12/2016 | Stanglmeier | G01N 27/4078 |
| 9,804,057 B2 * | 10/2017 | Stier | H02G 15/003 |

(Continued)

FOREIGN PATENT DOCUMENTS

| | | |
|---|---|---|
| JP | 2000509822 A | 8/2000 |
| JP | 4461585 B2 | 5/2010 |
| WO | 2019044746 A1 | 3/2019 |

OTHER PUBLICATIONS

Japanese Office Action received in corresponding Japanese Application No. 2019-155211 dated Dec. 15, 2022.

*Primary Examiner* — Joshua L Allen
*Assistant Examiner* — Shizhi Qian
(74) *Attorney, Agent, or Firm* — Mattingly & Malur, PC

(57) ABSTRACT

A gas sensor includes: a sensor element; a ceramic housing holding a rear end portion of the sensor element and provided with metal terminals electrically connected to the sensor element; and an elastic insulating member that is fixed in the rear of the sensor element and into which a plurality of lead wires electrically connected to the metal terminals are inserted. The elastic insulating member has one or more common spaces formed in a surface of the elastic insulating member that faces the ceramic housing. Two or more of the lead wires are arranged in each common space.

3 Claims, 4 Drawing Sheets

(56) References Cited

U.S. PATENT DOCUMENTS

| | | | |
|---|---|---|---|
| 2002/0003088 A1* | 1/2002 | Ozawa | G01N 27/4077 204/424 |
| 2015/0027888 A1* | 1/2015 | Soyez | G01N 27/4078 277/627 |
| 2015/0354997 A1 | 12/2015 | McCauley et al. | |
| 2020/0191743 A1 | 6/2020 | Ozawa | |

* cited by examiner

FIG. 4

[TABLE 1]

| CONDITION | SPACE (S) AT END OF GROMMET | RATIO OF SPACE (S) TO FULL LENGTH OF GROMMET [%] | NUMBER OF COMMON SPACES | NUMBER OF LEAD WIRES | JUDGMENT 1 | JUDGMENT 2 |
|---|---|---|---|---|---|---|
| EXAMPLE 1 | PRESENT | 30 | 1 | 8 | ○ | ○ |
| EXAMPLE 2 | PRESENT | 50 | 1 | 8 | ○ | ○ |
| EXAMPLE 3 | PRESENT | 80 | 1 | 8 | ○ | ○ |
| EXAMPLE 4 | PRESENT | 10 | 1 | 8 | ○ | ○ |
| EXAMPLE 5 | PRESENT | 30 | 2 | 6 | ○ | ○ |
| EXAMPLE 6 | PRESENT | 50 | 2 | 6 | ○ | ○ |
| EXAMPLE 7 | PRESENT | 80 | 2 | 6 | ○ | ○ |
| EXAMPLE 8 | PRESENT | 10 | 2 | 8 | ○ | ○ |
| EXAMPLE 9 | PRESENT | 30 | 2 | 8 | ○ | ○ |
| EXAMPLE 10 | PRESENT | 50 | 2 | 8 | ○ | ○ |
| EXAMPLE 11 | PRESENT | 80 | 2 | 6 | ○ | ○ |
| EXAMPLE 12 | PRESENT | 10 | 3 | 6 | ○ | ○ |
| EXAMPLE 13 | PRESENT | 30 | 3 | 6 | ○ | ○ |
| EXAMPLE 14 | PRESENT | 50 | 3 | 8 | ○ | ○ |
| EXAMPLE 15 | PRESENT | 80 | 4 | 8 | ○ | ○ |
| EXAMPLE 16 | PRESENT | 10 | 4 | 8 | ○ | ○ |
| EXAMPLE 17 | PRESENT | 30 | 4 | 8 | ○ | ○ |
| EXAMPLE 18 | PRESENT | 50 | 4 | 8 | ○ | ○ |
| EXAMPLE 19 | PRESENT | 80 | 4 | 8 | ○ | ○ |
| EXAMPLE 20 | PRESENT | 10 | 1 | 8 | ○ | ○ |
| EXAMPLE 21 | PRESENT | 5 | 1 | 8 | △ | ○ |
| COMPARATIVE EXAMPLE | ABSENT | — | — | 8 | × | × |

GAS SENSOR

CROSS-REFERENCE TO RELATED APPLICATION

This application is based upon and claims the benefit of priority from Japanese Patent Application No. 2019-155211 filed on Aug. 28, 2019, the contents of which are incorporated herein by reference.

BACKGROUND OF THE INVENTION

Field of the Invention

The present invention relates to a gas sensor.

Description of the Related Art

The technique disclosed in Japanese Patent No. 4461585 has an object to provide a gas sensor that is less prone to short circuits of lead wires, metal terminal members, etc. and that provides stable sensor output.

In order to achieve the object, the technique disclosed in Japanese Patent No. 4461585 adopts the following configuration. That is, the gas sensor includes first guide portions (531) formed at the front ends of individual first through holes in an elastic insulating member (5), and second guide portions (331) formed at the proximal ends of individual second through holes in an insulator (3). According to the gas sensor, the first guide portions (531) and the second guide portions (331) restrict movement of lead wires (161) and metal terminals (49).

SUMMARY OF THE INVENTION

The gas sensor described in Japanese Patent No. 4461585 has a space interposed between the ceramic housing and the elastic insulating member (grommet). Further, the plurality of lead wires from the sensor element are routed in the elastic insulating member through the guide portions (through holes). The number of the guide portions is the same as the number of the lead wires. The individual guide portions are separately formed from one end surface to the other end surface of the elastic insulating member.

However, though the space is interposed between the ceramic housing and the elastic insulating member, the end surface of the elastic insulating member on the sensor side is close to the ceramic housing. Furthermore, the end surface corresponds to the portion except the individually formed guide portions and therefore has a large area.

Accordingly, the heat conducted from the sensor element disposed on the distal side is easily transmitted to the elastic insulating member through the ceramic housing, and consequently there is a risk that erosion (dissolved loss) due to such heat will occur on the elastic insulating member.

The present invention has been devised considering the problem above, and an object of the present invention is to provide a gas sensor that can suppress temperature rise of the elastic insulating member to thereby reduce the risk of heat erosion (dissolution) of the elastic insulating member.

A gas sensor according to an aspect of the present invention includes:

a sensor element;

a ceramic housing holding a rear end portion of the sensor element and provided with metal terminals electrically connected to the sensor element; and an elastic insulating member that is fixed in the rear of the sensor element and into which a plurality of lead wires electrically connected to the metal terminals are inserted, wherein the elastic insulating member has one or more common spaces formed in a surface of the elastic insulating member that faces the ceramic housing, and two or more of the lead wires are arranged in each common space.

According to the present invention, it is possible to suppress temperature rise of the elastic insulating member and to thereby reduce the risk of erosion (dissolved loss) of the elastic insulating member caused by heat.

The above and other objects, features, and advantages of the present invention will become more apparent from the following description when taken in conjunction with the accompanying drawings, in which a preferred embodiment of the present invention is shown by way of illustrative example.

BRIEF DESCRIPTION OF THE DRAWINGS

FIG. 4 is Table 1 showing the results of evaluation of experiments for heat resistance and connection failure concerning examples 1 to 21 and a comparative example.

DESCRIPTION OF THE PREFERRED EMBODIMENTS

The gas sensor according to the present invention will be described below in detail in connection with preferred embodiments while referring to the accompanying drawings.

Figure 1:
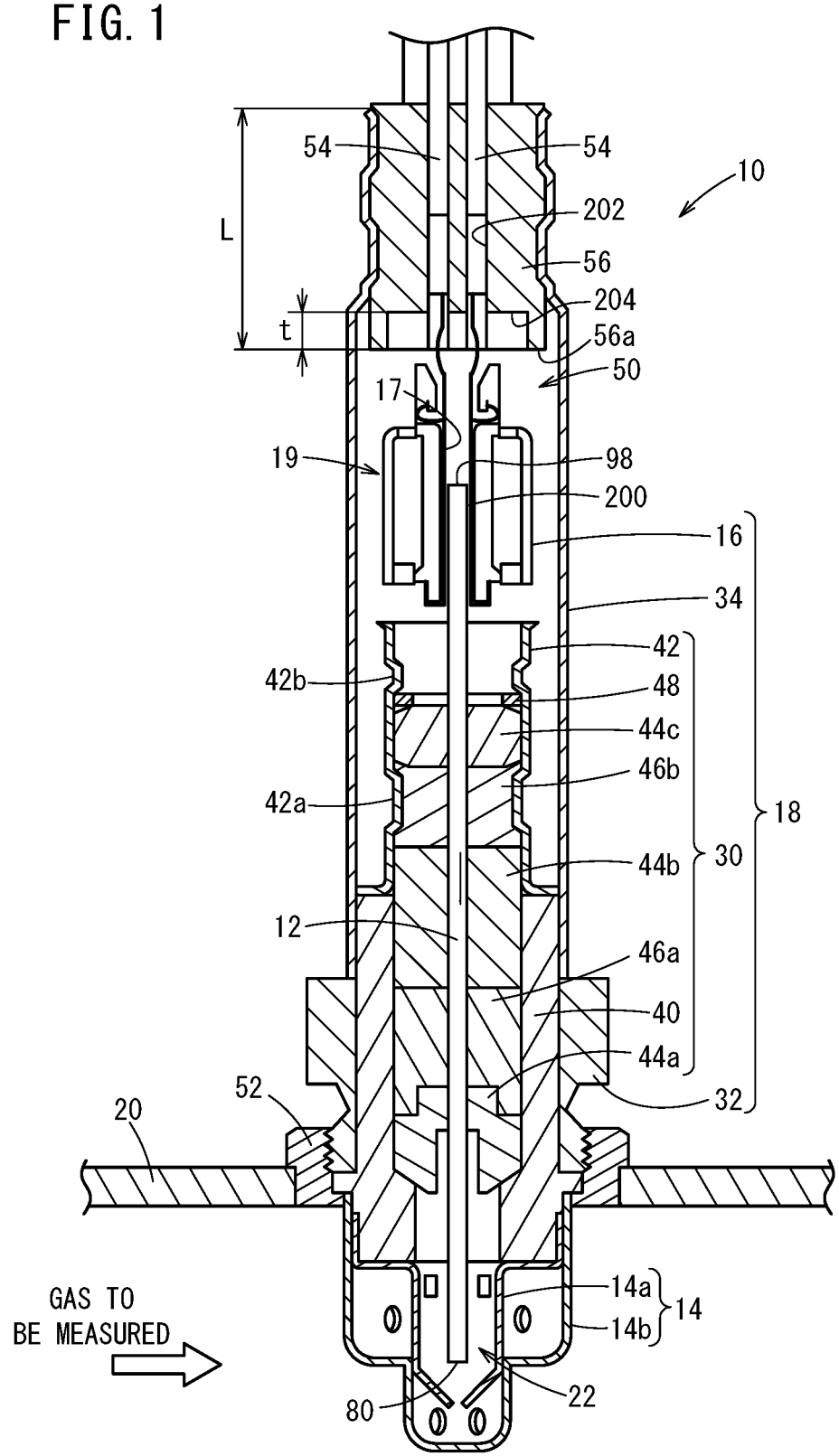
FIG. 1 is a cross section of a gas sensor according to an embodiment.

As shown in FIG. 1, a gas sensor 10 according to this embodiment includes a sensor element 12. The sensor element 12 has an elongated cuboidal shape or an elongated rectangular parallelepiped shape. The longitudinal direction of the sensor element 12 (the left-right direction in FIG. 2) is defined as a front-rear direction, and the thickness direction of the sensor element 12 (the up-down direction in FIG. 2) is defined as a top-bottom direction. The width direction of the sensor element 12 (a direction vertical to the front-rear and top-bottom directions) is defined as a left-right direction.

As shown in FIG. 1, the gas sensor 10 includes the sensor element 12, a protective cover 14 for protecting the front end of the sensor element 12, and a sensor assembly 18 including a ceramic housing 16. The ceramic housing 16 holds a rear end portion of the sensor element 12, and functions as a connector 19 when metal terminals 17 electrically connected to the sensor element 12 are attached thereto.

As shown in the drawing, the gas sensor 10 is attached to piping 20, such as an exhaust gas pipe of a vehicle, for example, and used to measure concentrations of specific gases, such as NOx, $O_2$, etc., that are contained in the exhaust gas as a gas to be measured.

The protective cover 14 includes a bottomed-tubular-shaped inner protective cover 14a covering the front end of the sensor element 12 and a bottomed-tubular-shaped outer protective cover 14b covering the inner protective cover 14a. The inner protective cover 14a and the outer protective cover 14b have formed therein a plurality of holes through which gas to be measured can flow into the interior of the protective cover 14. A sensor element chamber 22 is formed as a space enclosed by the inner protective cover 14a, and the front end of the sensor element 12 is disposed within the sensor element chamber 22.

The sensor assembly 18 includes an element seal body 30 for sealing and fixing the sensor element 12, and a nut 32 attached to the element seal body 30. The sensor assembly 18 includes an outer tube 34 and the connector 19, and the connector 19 is in contact with and is electrically connected to electrodes (not shown) that are formed on the surfaces (top and bottom surfaces) of the rear end of the sensor element 12.

The element seal body 30 includes a tubular main fitting 40, and a tubular, inner tube 42 that is welded and fixed coaxially with the main fitting 40. The element seal body 30 includes ceramic supporters 44a to 44c, green compacts (pressurized powder body) 46a, 46b, and a metal ring 48, which are sealed in an inner through hole in the interior of the main fitting 40 and the inner tube 42. The sensor element 12 is located on the center axis of the element seal body 30 and penetrates through the element seal body 30 in the front-rear direction. The inner tube 42 has a reduced-diameter portion 42a and a reduced-diameter portion 42b. The reduced-diameter portion 42a presses the green compact 46b toward the center axis of the inner tube 42. The reduced-diameter portion 42b presses frontward the ceramic supporters 44a to 44c and the green compacts 46a, 46b through the metal ring 48. The pressing forces from the reduced-diameter portions 42a, 42b compress the green compacts 46a, 46b between the main fitting 40 and inner tube 42 and the sensor element 12. The green compacts 46a, 46b thus provide a seal between the sensor element chamber 22 in the protective cover 14 and a space 50 in the outer tube 34 and fix the sensor element 12.

The nut 32 is fixed coaxially with the main fitting 40, and has a male thread portion formed on its outer peripheral surface. The male thread portion of the nut 32 is inserted into a fixing member 52 that is welded to the piping 20 and has a female thread formed on its inner peripheral surface. The gas sensor 10 is thus fixed to the piping 20 with the front end of the sensor element 12 and the protective cover 14 projecting into the piping 20.

The outer tube 34 encloses the inner tube 42, the sensor element 12, and the connector 19. A plurality of lead wires 54 connected to the connector 19 are led out from the rear end of the outer tube 34. The plurality of lead wires 54 electrically conduct through the connector 19 to electrodes of the sensor element 12 (which will be described later). The gap between the outer tube 34 and the lead wires 54 is sealed by an elastic insulating member 56 formed from grommet or the like. The space 50 in the outer tube 34 is filled with a reference gas (the air in this embodiment). The rear end of the sensor element 12 is disposed within this space 50.

Figure 2:
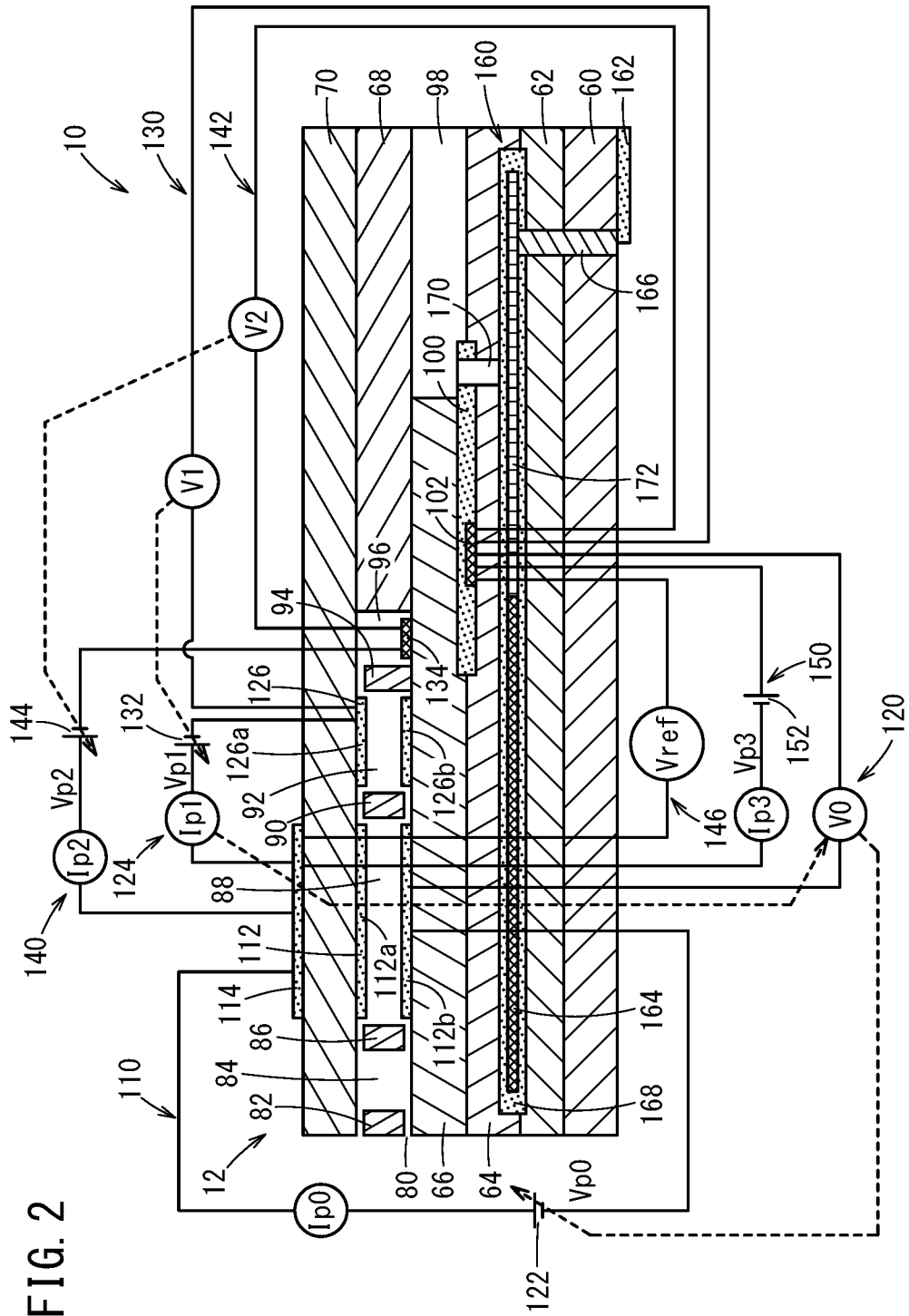
FIG. 2 is a schematic cross section schematically showing an exemplary configuration of a sensor element.

On the other hand, as shown in FIG. 2, the sensor element 12 is a device formed of a laminate in which six layers, for example, are laminated in this order from the bottom in the drawing. The six layers include a first substrate layer 60, a second substrate layer 62, a third substrate layer 64, a first solid electrolyte layer 66, a spacer layer 68, and a second solid electrolyte layer 70. The six layers are each formed of an oxygen ion conducting solid electrolyte layer, such as zirconia ($ZrO_2$), for example. In addition, the solid electrolyte forming the six layers is dense and gas-tight. The sensor element 12 is produced, for example, by applying given processing to, and printing circuit patterns on, ceramic green sheets corresponding to the respective layers, laminating these sheets together, and then integrating the sheets by sintering.

A plurality of diffusion control portions and a plurality of internal cavities, which will be described next, are formed between the lower surface of the second solid electrolyte layer 70 and the upper surface of the first solid electrolyte layer 66, on the side of one end of the sensor element 12 (on the left side in FIG. 2). That is, a gas inlet 80, a first diffusion control portion 82, a buffer space 84, a second diffusion control portion 86, a first internal cavity 88, a third diffusion control portion 90, a second internal cavity 92, a fourth diffusion control portion 94, and a third internal cavity 96 are formed in such a manner that they communicate and adjoin in this order.

The gas inlet 80, the buffer space 84, the first internal cavity 88, the second internal cavity 92, and the third internal cavity 96 are formed by hollowing out the spacer layer 68. Each of the buffer space 84 and others is a space in the sensor element 12 that is sectioned by the lower surface of the second solid electrolyte layer 70 at the top, the upper surface of the first solid electrolyte layer 66 at the bottom, and the side surfaces of the spacer layer 68 on the sides.

The first diffusion control portion 82, the second diffusion control portion 86, and the third diffusion control portion 90 are each formed as two horizontally-long slits (the openings thereof have their longitudinal direction in the direction vertical to the drawing sheet). The fourth diffusion control portion 94 is formed as one horizontally-long slit, which is formed as a gap below the lower surface of the second solid electrolyte layer 70 (the opening thereof has its longitudinal direction in the direction vertical to the drawing sheet). The section from the gas inlet 80 to the third internal cavity 96 will be referred to also as a measured gas passage.

A reference gas introduction space 98 is provided in a position separated farther from the above-mentioned one end, than the measured gas passage. The reference gas introduction space 98 is formed between the upper surface of the third substrate layer 64 and the lower surface of the spacer layer 68 and is sectioned by a side surface of the first solid electrolyte layer 66 on the side. A reference gas for the measurement of NOx concentration, e.g., the air (the atmosphere within the space 50 in FIG. 1), is introduced into the reference gas introduction space 98.

An atmosphere introduction layer 100 is a layer made of ceramic such as porous alumina etc., and is exposed to the reference gas introduction space 98. Reference gas is introduced to the atmosphere introduction layer 100 through the reference gas introduction space 98. The atmosphere introduction layer 100 is formed so as to cover a reference electrode 102. The atmosphere introduction layer 100 introduces the reference gas in the reference gas introduction space 98 to the reference electrode 102 while providing a given diffusion resistance to the reference gas. The atmosphere introduction layer 100 is formed in such a manner that it is exposed to the interior of the reference gas introduction space 98 only on a rear end side of the sensor element 12 that lies rearward of the reference electrode 102 (on the right side in FIG. 2). In other words, the reference gas introduction space 98 is not formed to a position right above the reference electrode 102. However, the reference electrode 102 may be formed right below the reference gas introduction space 98 in FIG. 2.

The reference electrode 102 is an electrode that is formed between the upper surface of the third substrate layer 64 and the first solid electrolyte layer 66, and, as mentioned above, the atmosphere introduction layer 100 connecting to the reference gas introduction space 98 is provided around it. The reference electrode 102 is formed directly on the upper surface of the third substrate layer 64 and is covered by the atmosphere introduction layer 100 except in portions contacting the upper surface of the third substrate layer 64. Also, as will be described later, it is possible to measure the oxygen concentrations (oxygen partial pressures) in the first internal cavity 88, the second internal cavity 92, and the third internal cavity 96, by using the reference electrode 102. The reference electrode 102 is formed as a porous cermet electrode (e.g., a cermet electrode of Pt and $ZrO_2$).

In the measured gas passage, the gas inlet 80 is opened to the outside space, and the measured gas is taken into the sensor element 12 from the outside space through the gas inlet. The first diffusion control portion 82 is a portion that provides a given diffusion resistance to the measured gas taken from the gas inlet 80. The buffer space 84 is a space that guides the measured gas introduced from the first diffusion control portion 82 to the second diffusion control portion 86. The second diffusion control portion 86 is a portion that provides a given diffusion resistance to the measured gas guided from the buffer space 84 into the first internal cavity 88. Now, a case will be described in which the measured gas is introduced from the outside of the sensor element 12 into the first internal cavity 88 by pressure fluctuation of the measured gas in the outside space. The pressure fluctuation can be caused by exhaust pressure pulsation if the measured gas is an automotive exhaust gas. The measured gas rapidly taken into the sensor element 12 from the gas inlet 80 due to pressure fluctuation is not directly introduced into the first internal cavity 88. Concentration variation of the measured gas is cancelled through the first diffusion control portion 82, the buffer space 84, and the second diffusion control portion 86, and then the measured gas is introduced into the first internal cavity 88. Accordingly, the concentration variation of the measured gas introduced into the first internal cavity 88 has become almost negligible. The first internal cavity 88 is a space that adjusts the oxygen partial pressure in the measured gas introduced through the second diffusion control portion 86. The oxygen partial pressure is adjusted by operation of a main pump cell 110 described next.

The main pump cell 110 is an electrochemical pump cell formed of an inside pumping electrode 112, an outside pumping electrode 114, and the second solid electrolyte layer 70. The inside pumping electrode 112 is provided on the internal surfaces of the first internal cavity 88. The outside pumping electrode 114 is formed on a portion of the upper surface of the second solid electrolyte layer 70 that corresponds to the inside pumping electrode 112 in such a manner that it is exposed to the outside space (the sensor element chamber 22 in FIG. 1). The second solid electrolyte layer 70 is sandwiched between the inside pumping electrode 112 and the outside pumping electrode 114.

The inside pumping electrode 112 is formed on the upper and lower solid electrolyte layers (the second solid electrolyte layer 70 and the first solid electrolyte layer 66) that section the first internal cavity 88, and on the spacer layer 68 that forms the side walls. Specifically, a ceiling electrode portion 112*a* of the inside pumping electrode 112 is formed on the lower surface of the second solid electrolyte layer 70 forming the ceiling surface of the first internal cavity 88. A bottom electrode portion 112*b* is formed directly on the upper surface of the first solid electrolyte layer 66 forming the bottom surface of the first internal cavity 88. Side electrode portions (not shown) are formed on the side wall surfaces (internal surfaces) of the spacer layer 68 forming both side walls of the first internal cavity 88, such that the side electrode portions connect the ceiling electrode portion 112*a* and the bottom electrode portion 112*b*. That is, the inside pumping electrode 112 is formed as a structure of a tunnel shape.

The inside pumping electrode 112 and the outside pumping electrode 114 are formed as porous cermet electrodes (e.g., cermet electrodes of Pt and $ZrO_2$ containing 1% Au). The inside pumping electrode 112 that contacts the measured gas is formed from a material with a weakened reduction capability to NOx components in the measured gas.

In the main pump cell 110, a desired pumping voltage Vp0 is applied across the inside pumping electrode 112 and the outside pumping electrode 114 to cause a pumping current Ip0 to flow in the positive direction or negative direction between the inside pumping electrode 112 and the outside pumping electrode 114. This enables the main pump cell 110 to pump out the oxygen in the first internal cavity 88 to the outside space, or to pump the oxygen in the outside space into the first internal cavity 88.

The sensor element 12 further includes a main-pump-controlling oxygen-partial-pressure-detecting sensor cell 120 for detecting the oxygen concentration (oxygen partial pressure) in the atmosphere in the first internal cavity 88. This sensor cell 120 is an electrochemical sensor cell including the inside pumping electrode 112, the second solid electrolyte layer 70, the spacer layer 68, the first solid electrolyte layer 66, and the reference electrode 102.

The oxygen concentration (oxygen partial pressure) in the first internal cavity 88 is known by measuring an electromotive force V0 in the main-pump-controlling oxygen-partial-pressure-detecting sensor cell 120. Further, the pumping current Ip0 is controlled by feedback controlling the pumping voltage Vp0 of a variable power supply 122 so as to keep the electromotive force V0 constant. The oxygen concentration in the first internal cavity 88 can thus be maintained at a certain constant value.

The third diffusion control portion 90 is a portion that provides a given diffusion resistance to the measured gas whose oxygen concentration (oxygen partial pressure) has been controlled by the operation of the main pump cell 110 in the first internal cavity 88, and that guides the gas to be measured, into the second internal cavity 92.

The second internal cavity 92 is provided as a space in which the measured gas, which has undergone oxygen concentration (oxygen partial pressure) adjustment in the first internal cavity 88 and is then introduced to the space through the third diffusion control portion 90, is subjected to further oxygen partial pressure adjustment by an auxiliary pump cell 124. The oxygen concentration in the second internal cavity 92 can thus be kept constant highly accurately, enabling the gas sensor 10 to perform highly accurate NOx concentration measurement.

The auxiliary pump cell 124 is an auxiliary electrochemical pump cell including an auxiliary pumping electrode 126 provided on the inner surfaces of the second internal cavity 92, the outside pumping electrode 114, and the second solid electrolyte layer 70. A suitable electrode outside of the sensor element 12 suffices as the outside pumping electrode 114.

The auxiliary pumping electrode 126 has a tunnel-shaped structure similar to that of the inside pumping electrode 112 provided in the first internal cavity 88 and is disposed in the second internal cavity 92. That is, a ceiling electrode portion 126*a* is formed on the second solid electrolyte layer 70 forming the ceiling surface of the second internal cavity 92. Also, a bottom electrode portion 126b is formed directly on the upper surface of the first solid electrolyte layer 66 forming the bottom surface of the second internal cavity 92. Then, side electrode portions (not shown) connecting the ceiling electrode portion 126a and the bottom electrode portion 126b are formed on both side surfaces of the spacer layer 68 forming the side walls of the second internal cavity 92, thus forming a tunnel-shaped structure. Like the inside pumping electrode 112, the auxiliary pumping electrode 126 is also made of a material having a weakened reduction capability to NOx components in the measured gas.

In the auxiliary pump cell 124, a desired voltage Vp1 is applied across the auxiliary pumping electrode 126 and the outside pumping electrode 114 so as to pump out the oxygen in the atmosphere in the second internal cavity 92 to the outside space, or to pump the oxygen into the second internal cavity 92 from the outside space.

Further, in order to control the oxygen partial pressure in the atmosphere in the second internal cavity 92, an electrochemical sensor cell, i.e., an auxiliary-pump-controlling oxygen-partial-pressure-detecting sensor cell 130, is formed of the auxiliary pumping electrode 126, the reference electrode 102, the second solid electrolyte layer 70, the spacer layer 68, and the first solid electrolyte layer 66.

The auxiliary pump cell 124 performs pumping with a variable power supply 132 that is voltage-controlled based on an electromotive force V1 detected by the auxiliary-pump-controlling oxygen-partial-pressure-detecting sensor cell 130. Thus, the oxygen partial pressure in the atmosphere in the second internal cavity 92 can be controlled to such low partial pressure as not to substantially affect the measurement of NOx.

In addition, a pumping current Ip1 thereof is used to control the electromotive force V0 of the main-pump-controlling oxygen-partial-pressure-detecting sensor cell 120. Specifically, the pumping current Ip1 is inputted as a control signal to the main-pump-controlling oxygen-partial-pressure-detecting sensor cell 120 to thereby control the electromotive force V0. Control is thus provided so that the gradient of oxygen partial pressure in the measured gas introduced from the third diffusion control portion 90 into the second internal cavity 92 can always be kept constant. When the gas sensor is used as a NOx sensor, the main pump cell 110 and the auxiliary pump cell 124 can operate to keep the oxygen concentration in the second internal cavity 92 at a constant value around about 0.001 ppm.

The fourth diffusion control portion 94 is a portion that provides a given diffusion resistance to the measured gas whose oxygen concentration (oxygen partial pressure) has been controlled in the second internal cavity 92 by the operation of the auxiliary pump cell 124, and that guides the measured gas into the third internal cavity 96. The fourth diffusion control portion 94 serves to limit the amount of NOx flowing into the third internal cavity 96.

The measured gas, whose oxygen concentration (oxygen partial pressure) has been adjusted in the second internal cavity 92, is introduced into the third internal cavity 96 through the fourth diffusion control portion 94. That is, the third internal cavity 96 is provided as a space in which the measured gas introduced therein is subjected to a process for the measurement of concentration of nitrogen oxide (NOx) in the measured gas. The measurement of NOx concentration is mainly performed in the third internal cavity 96 by operation of a measurement pump cell 140.

The measurement pump cell 140 measures the NOx concentration in the measured gas in the third internal cavity 96. The measurement pump cell 140 is an electrochemical pump cell formed of a measurement electrode 134 formed directly on the upper surface of the first solid electrolyte layer 66 facing the third internal cavity 96, the outside pumping electrode 114, the second solid electrolyte layer 70, the spacer layer 68, and the first solid electrolyte layer 66. The measurement electrode 134 is a porous cermet electrode. The measurement electrode 134 functions also as a NOx reduction catalyst that reduces the NOx present in the atmosphere in the third internal cavity 96.

In the measurement pump cell 140, the oxygen generated by the decomposition of nitrogen oxide in the atmosphere around the measurement electrode 134 is pumped out, and the amount of the generated oxygen can be detected as a pumping current Ip2.

Further, in order to detect the oxygen partial pressure around the measurement electrode 134, an electrochemical sensor cell, i.e., a measurement-pump-controlling oxygen-partial-pressure-detecting sensor cell 142, is formed of the first solid electrolyte layer 66, the measurement electrode 134, and the reference electrode 102. A variable power supply 144 is controlled based on an electromotive force V2 detected by the measurement-pump-controlling oxygen-partial-pressure-detecting sensor cell 142.

The measured gas guided into the second internal cavity 92 reaches the measurement electrode 134 in the third internal cavity 96 through the fourth diffusion control portion 94 in a state that the oxygen partial pressure is controlled. The nitrogen oxide in the measured gas around the measurement electrode 134 is reduced to generate oxygen ($2NO \rightarrow N_2+O_2$). Then, the oxygen generated is pumped by the measurement pump cell 140. In this process, a voltage Vp2 of the variable power supply 144 is controlled so that the electromotive force V2 detected by the measurement-pump-controlling oxygen-partial-pressure-detecting sensor cell 142 is kept constant. The amount of oxygen generated around the measurement electrode 134 is proportional to the concentration of the nitrogen oxide in the measured gas. Accordingly, the nitrogen oxide concentration in the measured gas is calculated using the pumping current Ip2 of the measurement pump cell 140.

Further, an electrochemical sensor cell 146 is formed of the second solid electrolyte layer 70, the spacer layer 68, the first solid electrolyte layer 66, the third substrate layer 64, the outside pumping electrode 114, and the reference electrode 102. The oxygen partial pressure in the measured gas outside of the sensor can be detected by an electromotive force Vref obtained by the sensor cell 146.

Further, an electrochemical reference-gas-adjustment pump cell 150 is formed of the second solid electrolyte layer 70, the spacer layer 68, the first solid electrolyte layer 66, the third substrate layer 64, the outside pumping electrode 114, and the reference electrode 102. The reference-gas-adjustment pump cell 150 performs pumping as a voltage Vp3 applied by a variable power supply 152 connected between the outside pumping electrode 114 and the reference electrode 102 causes a control current Ip3 to flow. The reference-gas-adjustment pump cell 150 thus pumps oxygen into a space (atmosphere introduction layer 100) around the reference electrode 102 from another space (the sensor element chamber 22 in FIG. 1) around the outside pumping electrode 114. The voltage Vp3 of the variable power supply 152 is predetermined as such a direct-current (DC) voltage that the control current Ip3 has a given value (a DC current with a constant value).

In the gas sensor 10 constructed as described above, the main pump cell 110 and the auxiliary pump cell 124 are operated so that the measurement pump cell 140 is supplied with the measured gas in which the oxygen partial pressure is always kept at a constant low value. The constant low value of oxygen partial pressure means a value that does not substantially affect the NOx measurement. Thus, the NOx concentration in the measured gas can be known based on the pumping current Ip2 that flows in substantially proportion to the NOx concentration in the measured gas as the oxygen generated by NOx reduction is pumped out by the measurement pump cell 140.

The sensor element 12 further includes a heater unit 160 that serves as a temperature controller by heating the sensor element 12 and keeping the temperature, in order to enhance the oxygen ion conductivity of the solid electrolyte. The heater unit 160 includes a heater connector electrode 162, a heater 164, a through hole 166, a heater insulating layer 168, a pressure release hole 170, and a lead wire 172.

The heater connector electrode 162 is an electrode that is formed in contact with the lower surface of the first substrate layer 60. The heater connector electrode 162 is connected to an external power supply to supply electricity to the heater unit 160 from outside.

The heater 164 is an electric resistor that is sandwiched between the second substrate layer 62 therebelow and the third substrate layer 64 thereabove. The heater 164 is connected to the heater connector electrode 162 through the lead wire 172 and the through hole 166. The heater 164 generates heat by being supplied with electricity from outside through the heater connector electrode 162, thereby heating the solid electrolyte forming the sensor element 12 and keeping it hot or warm.

Further, the heater 164 is buried in the entire area from the first internal cavity 88 to the third internal cavity 96, so that the entire sensor element 12 can be adjusted to temperatures at which the solid electrolyte is activated.

The heater insulating layer 168 is an insulating layer formed on the upper and lower surfaces of the heater 164, and it is made of porous alumina formed of an insulator of alumina etc. The heater insulating layer 168 is formed for the purpose of obtaining electric insulation between the second substrate layer 62 and the heater 164 and electric insulation between the third substrate layer 64 and the heater 164.

The pressure release hole 170 penetrates through the third substrate layer 64 to communicate with the reference gas introduction space 98, in order to reduce internal pressure increase caused by temperature rise in the heater insulating layer 168.

The variable power supplies 122, 144, 132, 152, etc. shown in FIG. 2 are actually connected to electrodes through lead wires (not shown) formed in the sensor element 12 and the connector 19 and lead wires 54 in FIG. 1.

In this embodiment, the metal terminals 17 extending rearward are electrically connected to corresponding connection terminals 200 that are exposed from the rear end portion of the sensor element 12. The ceramic housing 16 is provided around the rear end portion of the sensor element 12, and the metal terminals 17 are fitted in between the connection terminals 200 and the ceramic housing 16. The connection terminals 200 of the sensor element 12 and the metal terminals 17 are thus press fitted (crimped) and electrically connected together. That is, the ceramic housing 16 is provided with the metal terminals 17 electrically connected to the sensor element 12 and holds the rear end portion of the sensor element 12.

The rear portions of the metal terminals 17 extend rearward and beyond the ceramic housing 16 and are electrically connected, by solder etc., to the lead wires 54 inserted into the elastic insulating member 56. The elastic insulating member 56 has formed therein a plurality of through holes 202 along the axial direction of the sensor element 12. The lead wires 54 are inserted through the through holes 202, and the metal terminals 17 extending from the sensor element 12 and the lead wires 54 are electrically connected by solder etc.

In particular, as shown in FIGS. 3A to 3E, the gas sensor 10 of this embodiment has one or more spaces (referred to as a common space or common spaces 204) that are formed in a front end surface 56a of the elastic insulating member 56, each space containing two or more lead wires 54 (i.e., two or more lead wires are arranged in each space). The front end surface 56a is an end surface that faces toward the ceramic housing 16. As shown in FIG. 1, a depth "t" of the common space(s) 204 is from 10 to 80% relative to a full length L of the elastic insulating member 56.

Figure 3A:
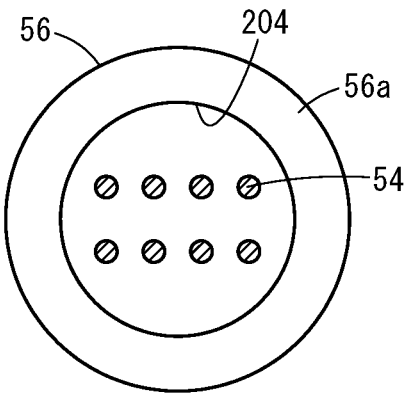
FIGS. 3A, 3B, 3C, 3D, and 3E are diagrams showing exemplary combinations of common space(s) and lead wires that are formed in an elastic insulating member.
Figure 3B:
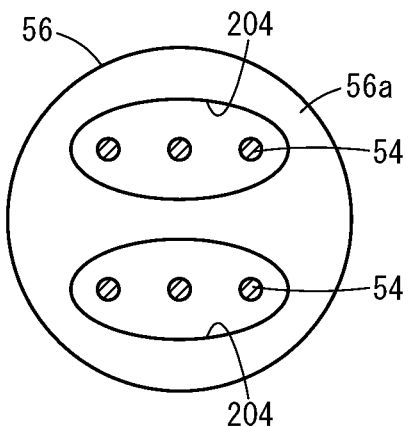
Figure 3C:
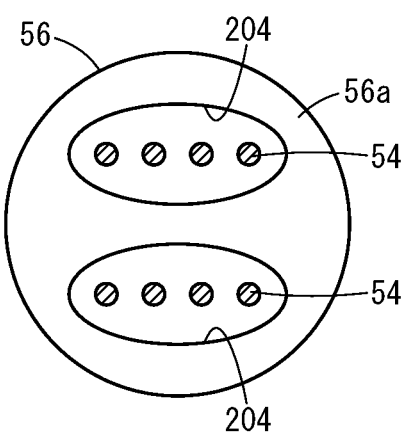
Figure 3D:
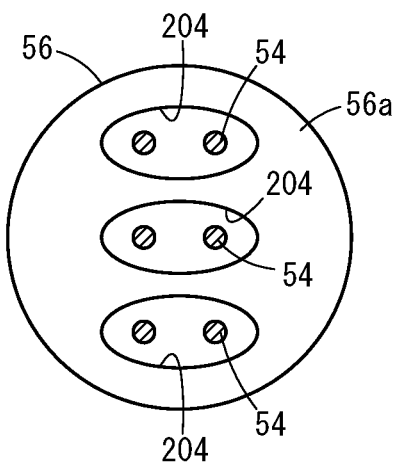
Figure 3E:
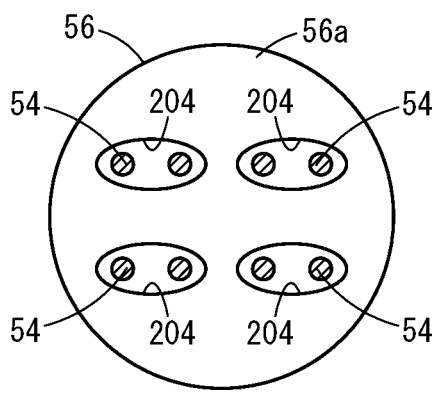

FIG. 3A shows a first structure in which eight lead wires 54 are inserted in one common space 204 (eight lead wires 54 in total). FIG. 3B shows a second structure in which three lead wires 54 are inserted in each of two common spaces 204 (six lead wires 54 in total). FIG. 3C shows a third structure in which four lead wires 54 are inserted in each of two common spaces 204 (eight lead wires 54 in total). FIG. 3D shows a fourth structure in which two lead wires 54 are inserted in each of three common spaces 204 (six lead wires 54 in total). FIG. 3E shows a fifth structure in which two lead wires 54 are inserted in each of four common spaces 204 (eight lead wires 54 in total). These structures are shown only by way of example and various structures are of course possible. For example, FIGS. 3B to 3E illustrate examples in which the longer axis of the common spaces 204 extends laterally, but the longer axis may extend vertically or obliquely.

By adopting any of the first to fifth structures above, it is possible to prevent erosion (dissolution) of the elastic insulating member 56 and to reduce contact failure (connection failure) at connections. That is, it is possible to suppress temperature rise of the elastic insulating member 56 and improve heat resistance of the gas sensor 10.

Now, experiment examples will be shown in which heat resistance and connection failure were evaluated concerning examples 1 to 21 and a comparative example. A rubber grommet was used as the elastic insulating member 56.

EXAMPLE 1

The gas sensor of example 1 has a common space 204 in the front end surface 56a of the elastic insulating member 56, and the depth t of the common space 204 is 30% of the full length L of the elastic insulating member 56. The number of common space 204 is one and the number of lead wires 54 is eight, and the gas sensor thus has the first structure shown in FIG. 3A.

EXAMPLE 2

The gas sensor of example 2 has a common space 204 in the front end surface 56a of the elastic insulating member 56 and the depth t of the common space 204 is 50% of the full length L of the elastic insulating member 56. Like example 1, the gas sensor thus has the first structure shown in FIG. 3A.

EXAMPLE 3

The gas sensor of example 3 has a common space 204 in the front end surface 56a of the elastic insulating member 56 and the depth t of the common space 204 is 80% of the full length L of the elastic insulating member 56. Like example 1, the gas sensor thus has the first structure shown in FIG. 3A.

EXAMPLE 4

The gas sensor of example 4 has a common space 204 in the front end surface 56*a* of the elastic insulating member 56 and the depth t of the common space 204 is 10% of the full length L of the elastic insulating member 56. Like example 1, the gas sensor thus has the first structure shown in FIG. 3A.

EXAMPLE 5

The gas sensor of example 5 has common spaces 204 in the front end surface 56*a* of the elastic insulating member 56 and the depth t of the common spaces 204 is 30% of the full length L of the elastic insulating member 56. The number of common spaces 204 is two and the number of lead wires 54 is six, and the gas sensor thus has the second structure shown in FIG. 3B.

EXAMPLE 6

The gas sensor of example 6 has common spaces 204 in the front end surface 56*a* of the elastic insulating member 56 and the depth t of the common spaces 204 is 50% of the full length L of the elastic insulating member 56. Like example 5, the gas sensor thus has the second structure shown in FIG. 3B.

EXAMPLE 7

The gas sensor of example 7 has common spaces 204 in the front end surface 56*a* of the elastic insulating member 56 and the depth t of the common spaces 204 is 80% of the full length L of the elastic insulating member 56. Like example 5, the gas sensor thus has the second structure shown in FIG. 3B.

EXAMPLE 8

The gas sensor of example 8 has common spaces 204 in the front end surface 56*a* of the elastic insulating member 56 and the depth t of the common spaces 204 is 10% of the full length L of the elastic insulating member 56. Like example 5, the gas sensor thus has the second structure shown in FIG. 3B.

EXAMPLE 9

The gas sensor of example 9 has common spaces 204 in the front end surface 56*a* of the elastic insulating member 56 and the depth t of the common spaces 204 is 30% of the full length L of the elastic insulating member 56. The number of common spaces 204 is two and the number of lead wires 54 is eight, and the gas sensor thus has the third structure shown in FIG. 3C.

EXAMPLE 10

The gas sensor of example 10 has common spaces 204 in the front end surface 56*a* of the elastic insulating member 56 and the depth t of the common spaces 204 is 50% of the full length L of the elastic insulating member 56. Like example 9, the gas sensor thus has the third structure shown in FIG. 3C.

EXAMPLE 11

The gas sensor of example 11 has common spaces 204 in the front end surface 56*a* of the elastic insulating member 56 and the depth t of the common spaces 204 is 80% of the full length L of the elastic insulating member 56. Like example 9, the gas sensor thus has the third structure shown in FIG. 3C.

EXAMPLE 12

The gas sensor of example 12 has common spaces 204 in the front end surface 56*a* of the elastic insulating member 56 and the depth t of the common spaces 204 is 10% of the full length L of the elastic insulating member 56. Like example 9, the gas sensor thus has the third structure shown in FIG. 3C.

EXAMPLE 13

The gas sensor of example 13 has common spaces 204 in the front end surface 56*a* of the elastic insulating member 56 and the depth t of the common spaces 204 is 30% of the full length L of the elastic insulating member 56. The number of common spaces 204 is three and the number of lead wires 54 is six, and the gas sensor thus has the fourth structure shown in FIG. 3D.

EXAMPLE 14

The gas sensor of example 14 has common spaces 204 in the front end surface 56*a* of the grommet of the elastic insulating member 56 and the depth t of the common spaces 204 is 50% of the full length L of the elastic insulating member 56. Like example 13, the gas sensor thus has the fourth structure shown in FIG. 3D.

EXAMPLE 15

The gas sensor of example 15 has common spaces 204 in the front end surface 56*a* of the elastic insulating member 56 and the depth t of the common spaces 204 is 80% of the full length L of the elastic insulating member 56. Like example 13, the gas sensor thus has the fourth structure shown in FIG. 3D.

EXAMPLE 16

The gas sensor of example 16 has common spaces 204 in the front end surface 56*a* of the elastic insulating member 56 and the depth t of the common spaces 204 is 10% of the full length L of the elastic insulating member 56. Like example 13, the gas sensor thus has the fourth structure shown in FIG. 3D.

EXAMPLE 17

The gas sensor of example 17 has common spaces 204 in the front end surface 56*a* of the elastic insulating member 56 and the depth t of the common spaces 204 is 30% of the full length L of the elastic insulating member 56. The number of common spaces 204 is four and the number of lead wires 54 is eight, and the gas sensor thus has the fifth structure shown in FIG. 3E.

EXAMPLE 18

The gas sensor of example 18 has common spaces 204 in the front end surface 56a of the elastic insulating member 56 and the depth t of the common spaces 204 is 50% of the full length L of the elastic insulating member 56. Like example 17, the gas sensor thus has the fifth structure shown in FIG. 3E.

EXAMPLE 19

The gas sensor of example 19 has common spaces 204 in the front end surface 56a of the elastic insulating member 56 and the depth t of the common spaces 204 is 80% of the full length L of the elastic insulating member 56. Like example 17, the gas sensor thus has the fifth structure shown in FIG. 3E.

EXAMPLE 20

The gas sensor of example 20 has common spaces 204 in the front end surface 56a of the elastic insulating member 56 and the depth t of the common spaces 204 is 10% of the full length L of the elastic insulating member 56. Like example 17, the gas sensor thus has the fifth structure shown in FIG. 3E.

EXAMPLE 21

The gas sensor of example 21 has a common space 204 in the front end surface 56a of the elastic insulating member 56 and the depth t of the common space 204 is 5% of the full length L of the elastic insulating member 56. Like example 1, the gas sensor thus has the first structure shown in FIG. 3A.

Comparative Example

The gas sensor of the comparative example does not have any common space 204 in the front end surface 56a of the elastic insulating member 56. The number of lead wires 54 is eight.

Evaluation Method

Presence/absence of erosion (dissolved loss) of the elastic insulating member 56 and presence/absence of connection failure were evaluated after a heating and vibration test.

Experiment Method

The gas sensor was attached to a chamber in which a high-temperature gas at 900° C. flows, and a test was conducted for 150 hours under the vibration conditions below.

Frequency: 50, 100, 150, 250 Hz
Acceleration: 30 G, 40 G, 50 G
Sweep time: 30 min./sweep cycle
Testing time: 150 hours
Gas temperature: 900° C.

Judgement 1: Presence/Absence of Erosion of Grommet

Vref signal was monitored during the test to see whether the Vref signal changed to exceed a given threshold. The Vref signal exceeding the given threshold means that the elastic insulating member 56 eroded to thereby generate gas, and as a result, the oxygen concentration around the reference electrode 102 decreased.

Criteria for judgement were set as follows.
o: The Vref signal did not exceed the given threshold during the durability test.
Δ: The Vref signal exceeded the given threshold in 50 to 150 hours.
x: The Vref signal exceeded the given threshold within 50 hours.

Judgment 2: Presence/Absence of Connection Failure Through Test

Criteria for judgment were set as follows.
o: Connection failure absent
x: Connection failure present Table 1 of FIG. 4 shows the results of evaluation. It is seen from the results of evaluation shown in table 1 that good results were obtained concerning both the judgment 1 and judgment 2 both in the cases where a common space or common spaces 204 having a depth t of 10% to 80% relative to the full length L of the elastic insulating member 56 were present in the front end surface 56a of the elastic insulating member 56.

Example 21 in which the depth t was less than 10% of the full length L of the elastic insulating member 56 showed a good result about judgment 2 but an inferior result about judgment 1.

The comparative example where no common space 204 was present in the front end surface 56a of the elastic insulating member 56 showed poor results about both judgments 1 and 2.

From these results, it is understood that the presence of a common space or spaces 204 in the front end surface 56a of the elastic insulating member 56 is preferred and that the formation of the common space or spaces 204 in the range from 10% to 80% of the full length L of the elastic insulating member 56 is more preferred.

Further, the presence of a plurality of common spaces 204 facilitates positioning for electrically connecting the lead wires 54 and the metal terminals 17 extending from the gas sensor, and it is possible to reduce the number of process steps and man-hours.

Invention Obtained from Embodiments

The embodiments described above can be summarized as follows.

[1] A gas sensor 10 according to the embodiment includes: a sensor element 12; a ceramic housing 16 holding a rear end portion of the sensor element 12 and provided with metal terminals 17 electrically connected to the sensor element 12; and an elastic insulating member 56 that is fixed in the rear of the sensor element 12 and into which a plurality of lead wires 54 electrically connected to the metal terminals 17 are inserted. The elastic insulating member 56 has one or more common spaces 204 formed in a surface (front end surface 56a) of the elastic insulating member 56 that faces the ceramic housing 16, and two or more of the lead wires 54 are arranged in each common space 204.

It is thus possible to suppress temperature rise of the elastic insulating member 56. As a result, it is possible to reduce the risk of erosion (dissolved loss) of the elastic insulating member 56 due to heat and to prevent the occurrence of disconnection and connection failure around connections due to vibration and the like.

[2] In this embodiment, the one or more common spaces 204 have a length (depth t) in a depth direction thereof which is 10 to 80% of the full length L of the elastic insulating member 56. It is thus possible to prevent erosion of the elastic insulating member 56 at the end thereof that is prone to temperature rise.

[3] In this embodiment, the one or more common spaces 204 include two or more common spaces. Presence of a plurality of common spaces 204 facilitates positioning for electrically connecting the lead wires 54 and the metal terminals 17 extending from the gas sensor 10 and reduces the number of process steps and man-hours.

[4] In this embodiment, the one or more common spaces 204 have a length (depth t) in a depth direction thereof which is 10 to 80% of the full length L of the elastic insulating member 56, and the one or more common spaces 204 include two or more and four or less common spaces 204.

It is thus possible to prevent erosion (dissolved loss) of the elastic insulating member 56 at a distal end thereof that is prone to temperature rise and to reduce heat conduction from the lead wires 54 and prevent disconnection and connection failure from occurring around connections due to vibration or the like.

The embodiments described above have illustrated the sensor element 12 used to detect the NOx concentration in the measured gas, but the application thereof is not limited thereto as long as the sensor element 12 can be applied to detect concentration of another specific gas in the measured gas. For example, the sensor element 12 may detect the oxygen concentration in the measured gas.

Implementations of the present invention may be provided with various further means to improve reliability as an automotive component without departing from the idea of the present invention.

The present invention is not particularly limited to the embodiment described above, and various modifications are possible without departing from the essence and gist of the present invention.

What is claimed is:

1. A gas sensor comprising:
   a sensor element;
   a ceramic housing holding a rear end portion of the sensor element and provided with metal terminals electrically connected to the sensor element; and
   an elastic insulating member that is fixed in a rear of the gas sensor and into which a plurality of lead wires electrically connected to the metal terminals are inserted,
   wherein the elastic insulating member has two or more common spaces that are two or more recesses formed in a surface of the elastic insulating member, the surface of the elastic insulating member facing the ceramic housing, and three or more of the lead wires are arranged in each common space.

2. The gas sensor according to claim 1, wherein the two or more common spaces each have a length in a depth direction thereof which is 10 to 80% of a full length of the elastic insulating member.

3. The gas sensor according to claim 2, wherein the two or more common spaces comprise two or more and four or less common spaces.

* * * * *